United States Patent
Powell

[11] Patent Number: 5,547,465
[45] Date of Patent: Aug. 20, 1996

[54] FINGER PATCH WITH ADHESIVE BACKING

[76] Inventor: Dorothy J. Powell, 4839 So. Vancouver, Tulsa, Okla. 74107

[21] Appl. No.: 833,666

[22] Filed: Feb. 11, 1992

[51] Int. Cl.[6] .......................... A61F 13/00; A61F 15/00
[52] U.S. Cl. ................................. 602/54; 602/41
[58] Field of Search .................. 602/41, 52, 54, 602/58; 128/888, 889, 857, 890, 892–893; 2/21, 161 R; 206/460; 15/227

[56] References Cited

U.S. PATENT DOCUMENTS

| | | | |
|---|---|---|---|
| 2,619,961 | 12/1952 | Stewart | 128/894 |
| 2,763,885 | 9/1956 | Lyons | 15/227 |
| 3,283,888 | 11/1966 | Scott . | |
| 3,548,420 | 12/1970 | Spence | 128/889 |
| 3,594,813 | 7/1971 | Sanderson | 128/857 |
| 3,905,113 | 9/1975 | Jacob | 433/216 |
| 4,890,608 | 1/1990 | Steer | 602/57 |
| 5,172,424 | 12/1992 | Adkins | 2/21 |

Primary Examiner—Mary Beth Jones
Assistant Examiner—P. Zuttarelli
Attorney, Agent, or Firm—Young & Thompson

[57] ABSTRACT

A finger patch with a pressure-sensitive adhesive backing, is a molded solid rubber body which is concave in the undeformed condition, and has a relatively thick mid-portion and a relatively thin edge entirely surrounding the body. The outer surface of the edge is disposed at an acute angle to the underside of the body that contacts the fingertip of the user, thereby to avoid catching of the patch on the edges of papers handled by the user. The patch has a thickness of the thickened mid-portion of 0.023 to 0.049 inch, a Shore "A" hardness of 43–47 and a concavity of about ⅛ inch in its undeformed condition. A release paper covers the pressure-sensitive adhesive, the finger patch being oval and the release paper having a tail that extends from only one end of the oval finger patch.

5 Claims, 1 Drawing Sheet

FIG. 1
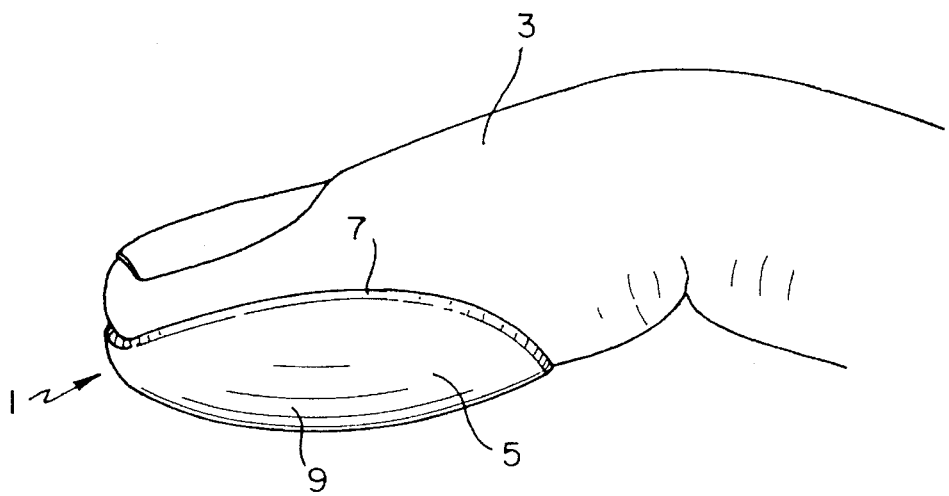
FIG. 2
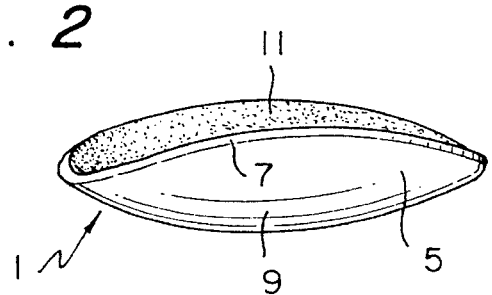
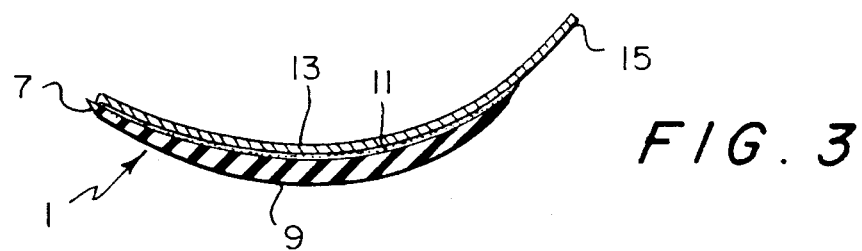
FIG. 3

5,547,465

FINGER PATCH WITH ADHESIVE BACKING

FIELD OF THE INVENTION

The present invention relates to a finger patch with an adhesive backing, for use in the handling of papers.

BACKGROUND OF THE INVENTION

When handling papers, the tips of the fingers become dry and slippery and it is difficult to separate individual sheets of paper from each other.

In the past, this has been remedied by wetting the fingers by licking them, which is of course unsanitary and repellent to the observer.

Another solution proposed in the past has been to provide an artificial substance which increases the friction of the fingers. It is necessary to apply this substance to the fingertips from time to time; and in addition to the inconvenience of doing this, there is the drawback that the material tends to transfer to the paper, thus soiling the paper. Also, the fingers must be washed after using this material, and of course certain persons are sensitive to the material thus applied to the fingers.

A very common expedient is to use a finger cot or stall. However, these devices completely enclose the end of the finger and cause unfavorable reactions in a large number of users, even to the point of the loss of a fingernail.

THE KNOWN PRIOR ART

Scott, U.S. Pat. No. 3,283,888, which issued Nov. 8, 1966, proposes a solution to the problem in the form of a patch of foam rubber that is secured to the ball of the fingertip by pressure-sensitive adhesive. The patch is provided with a release sheet to cover the pressure-sensitive adhesive until the time of use.

The patch of the Scott patent is made of foam rubber and is evidently cut from a sheet of foam rubber to the appropriate size and shape, and so can be circular or oval, of various sizes. Because it is evidently cut from a sheet, the foam rubber of Scott is of uniform thickness throughout and has edges perpendicular to its major faces.

A number of disadvantages inhere in the Scott device. In the first place, because it is of foam rubber, it is very pliable. In order to handle it without deforming it so that the adhesive surface sticks to itself, and so that it can be easily applied to the fingertip, it must be of substantial thickness. But if of substantial thickness, then when it conforms to the shape of the fingertip, it wrinkles. Making the Scott device thinner would not cure this, because if the Scott device were much thinner, then it would be difficult to handle successfully, for the reasons given above.

Moreover, the edges of the Scott device have a tendency to catch on the edges of papers. Again, making the edges thinner would not cure this, because it is difficult to manipulate an undesirably thin device according to Scott.

OBJECTS OF THE INVENTION

It is accordingly an object of the present invention to provide a finger patch with adhesive backing, which is desirably thin but at the same time has sufficient resistance to bending to make it easily manipulable.

Another object of the present invention is the provision of a finger patch that conforms to the fingertip without wrinkling.

Still another object of the present invention is the provision of a finger patch which will not catch on the edge of papers.

Finally, it is another object of the present invention to provide a finger patch which will be relatively simple and inexpensive to manufacture, easy to manipulate, and rugged and durable in use.

BRIEF DESCRIPTION OF THE DRAWINGS

Other objects, features and advantages of the present invention will become apparent from a consideration of the following description, taken in connection with the accompanying drawing, in which:

FIG. 1 is a side elevational view of a finger patch with adhesive backing, according to the present invention, in use.

FIG. 2 is a perspective view of the finger patch itself, in the condition in which it is applied to the fingertip; and FIG. 3 is an enlarged cross-sectional view of a finger patch with adhesive backing according to the invention, in the condition in which it is sold, before it is readied for use.

DETAILED DESCRIPTION OF THE INVENTION

According to the present invention, and as shown first in FIG. 1 of the accompanying drawing, there is provided a finger patch with adhesive backing shown generally at 1, for application to the ball of the tip of a finger 3 to increase the friction of the fingertip for the purpose of handling paper.

Patch 1 comprises a body 5 which is of solid pure natural gum rubber, preferably having a Shore "A" hardness of 43–47 and a thickness of 0.023–0.049 inch. Body 5 is formed by molding and is concave, which is to say upwardly concave as shown in the drawing, with a concavity, that is, a sagitta, of about ⅛ inch in its unstressed and undeformed condition.

Body 5 is of a thickness that varies from edge to edge, and is entirely surrounded by a thin edge 7 which can be bevelled or gently rounded so as not to present any abrupt edge against which the edge of the paper can catch. The thickness of body 5 increases progressively inwardly from edge 7 to a thickened mid-portion 9.

A layer 11 of pressure-sensitive adhesive covers the concave, that is the inner surface of body 5 and can be the type of acrylic pressure-sensitive adhesive found on double-coated tape, although all manner of pressure-sensitive adhesive can be used provided it is not known to produce allergic reactions in contact with human skin.

Layer 11 of pressure-sensitive adhesive is covered with a release paper 13 of conventional type, which protects the pressure-sensitive adhesive until the patch is used and which can be peeled off immediately prior to application to the fingertip. To facilitate peeling off the release paper, the release paper is provided with a tail 15 at only one end of the elongated oval finger patch 1. It is preferred that the release paper 13 not extend beyond edge 7 of the finger patch except at tail 15 so as to avoid unsightly wrinkling of the release paper and for purposes of economy.

Because the mid-portion 9 is thickened, when the release paper is removed the patch will still have sufficient resistance to bending that it can be easily manipulated without areas of the pressure-sensitive adhesive sticking to each other. But at the same time, because edge 7 is thin, the finger patch will not catch on the edges of papers in use.

Because the finger patch of the present invention is molded, it does not have to flex to adapt to the shape of the user's finger, and hence has an increased tendency to stay in place and to avoid wrinkling.

Because the finger patch of the present invention is made of solid rubber rather than foam rubber, it can be made desirably thin at edge 7 without becoming mis-positioned upon application to the fingertip, because of course per unit of thickness, the solid molded rubber has increased rigidity compared to foam rubber.

From a consideration of the foregoing disclosure, therefore, it will be evident that all the initially recited objects of the present invention have been achieved.

Although the present invention has been described and illustrated in connection with the preferred embodiment, it is to be understood that modifications and variations may be resorted to without departing from the spirit of the invention, as those skilled in this art will readily understand. Such modifications and variations are considered to be within the purview and scope of the present invention as defined by the appended claims.

What is claimed is:

1. A finger patch consisting of a molded solid rubber body which is concave in an undeformed condition, and has a relatively thick mid-portion tapering to a relatively thin edge entirely peripherally bounding said body, a concave side of said body that contacts a finger tip of a user meeting a convex opposite side of said body at an acute angle at the said edge entirely peripherally about said body, thereby to avoid catching of the patch on edges of papers handled by a user, and a pressure-sensitive adhesive coating said concave side of said body.

2. A finger patch with pressure-sensitive adhesive backing as claimed in claim 1, in which the finger patch has a thickness of said relatively thick mid-portion of 0.023 to 0.049 inch, a Shore "A" hardness of 43–47 and a sagitta of about ⅛ inch in its undeformed condition.

3. A finger patch with pressure-sensitive adhesive backing as claimed in claim 1, in which the finger patch has a thickness of said relatively thick mid-portion of 0.023 to 0.049 inch.

4. A finger patch with pressure-sensitive adhesive backing as claimed in claim 1, that has a Shore "A" hardness of 43–47.

5. A finger patch with pressure-sensitive adhesive backing as claimed in claim 1, that has a sagitta of about one-eighth inch in its undeformed condition.

* * * * *